United States Patent
Pardo et al.

(10) Patent No.: US 7,206,642 B2
(45) Date of Patent: *Apr. 17, 2007

(54) IMPLANTABLE LEAD WITH IMPROVED STYLET LUMEN

(75) Inventors: Xavier E. Pardo, Minneapolis, MN (US); Brian T. Stolz, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 502 days.

This patent is subject to a terminal disclaimer.

(21) Appl. No.: 10/131,559

(22) Filed: Apr. 22, 2002

(65) Prior Publication Data

US 2003/0199954 A1    Oct. 23, 2003

(51) Int. Cl.
    *A61N 1/00*    (2006.01)
(52) U.S. Cl. .................................... 607/116
(58) Field of Classification Search ............. 607/122, 607/116–128, 101; 606/41, 47; 600/373–375; 604/103, 164.11
    See application file for complete search history.

(56) References Cited

U.S. PATENT DOCUMENTS

| | | |
|---|---|---|
| 1,674,804 A | 6/1928 | Stearns |
| 3,289,149 A | 11/1966 | Pawloski |
| 3,565,074 A * | 2/1971 | Foti ............... 604/164.11 |
| 4,207,900 A * | 6/1980 | Patel et al. ........... 604/103 |
| 4,325,599 A | 4/1982 | Feldman |
| 4,335,930 A | 6/1982 | Feldman |
| 4,777,955 A * | 10/1988 | Brayton et al. ......... 600/374 |
| 4,835,853 A | 6/1989 | Hirschberg |
| 4,920,980 A | 5/1990 | Jackowski |
| 5,170,787 A | 12/1992 | Lindegren ............. 128/642 |
| 6,110,146 A | 8/2000 | Berthiaume et al. ...... 604/160 |
| 6,181,971 B1 | 1/2001 | Doan |
| 6,216,045 B1 | 4/2001 | Black et al. |
| 6,295,990 B1 | 10/2001 | Lewis et al. ............ 128/898 |
| 6,435,189 B1 | 8/2002 | Lewis et al. ............ 128/898 |
| 6,436,087 B1 | 8/2002 | Lewis et al. ............ 604/508 |
| 6,456,889 B2 * | 9/2002 | Pianca et al. ........... 607/122 |
| 6,456,890 B2 | 9/2002 | Pianca et al. ........... 607/122 |
| 6,481,439 B1 | 11/2002 | Lewis et al. ............ 128/898 |
| 6,522,932 B1 * | 2/2003 | Kuzma et al. ........... 607/116 |
| 6,766,203 B2 * | 7/2004 | Doan et al. ............. 607/122 |
| 6,792,317 B1 | 9/2004 | Doan et al. ............. 607/122 |
| 2001/0037135 A1 | 11/2001 | Pianca et al. ........... 607/122 |
| 2001/0037136 A1 | 11/2001 | Pianca et al. ........... 607/122 |
| 2003/0023230 A1 | 1/2003 | Lewis et al. ............ 604/537 |

FOREIGN PATENT DOCUMENTS

| | | |
|---|---|---|
| DE | SW 0070446 | 10/1930 |
| EP | 0 450 181 A1 | 10/1991 |
| WO | WO/0069323 | 11/2000 |

* cited by examiner

*Primary Examiner*—George Manuel
(74) *Attorney, Agent, or Firm*—Fredrikson & Byron, P.A.

(57) ABSTRACT

An implantable lead for a medical device with an improved stylet lumen reduces the potential for damage to a stylet and seals the lead proximal end. The implantable lead comprises a lead body having a distal end and a proximal end, a stylet lumen, at least two conductor lumens, at least two conductors, at least two contacts carried on the proximal end, at least two contacts carried on the distal end, and a proximal flare formed on the lead proximal end. The two conductors are contained in the conductor lumens and extend from the lead proximal end to the distal end. The two contacts carried on the lead distal end are electrically connected to the conductors. The proximal flare has tapering walls that narrow toward a stylet opening to guide insertion of a stylet into the stylet lumen, and the proximal flare seals the conductor lumens proximal end to isolate the conductor lumens.

33 Claims, 11 Drawing Sheets

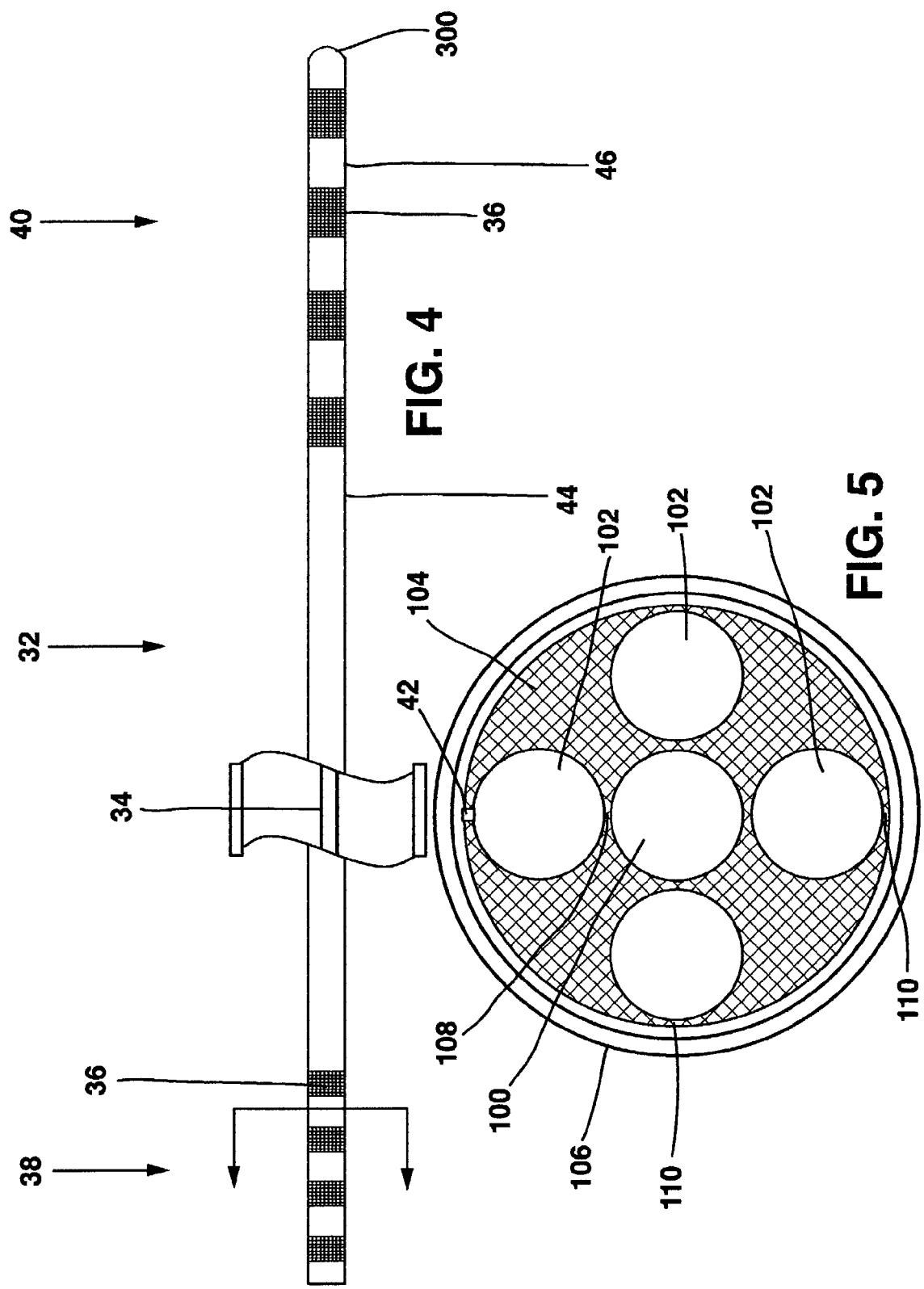

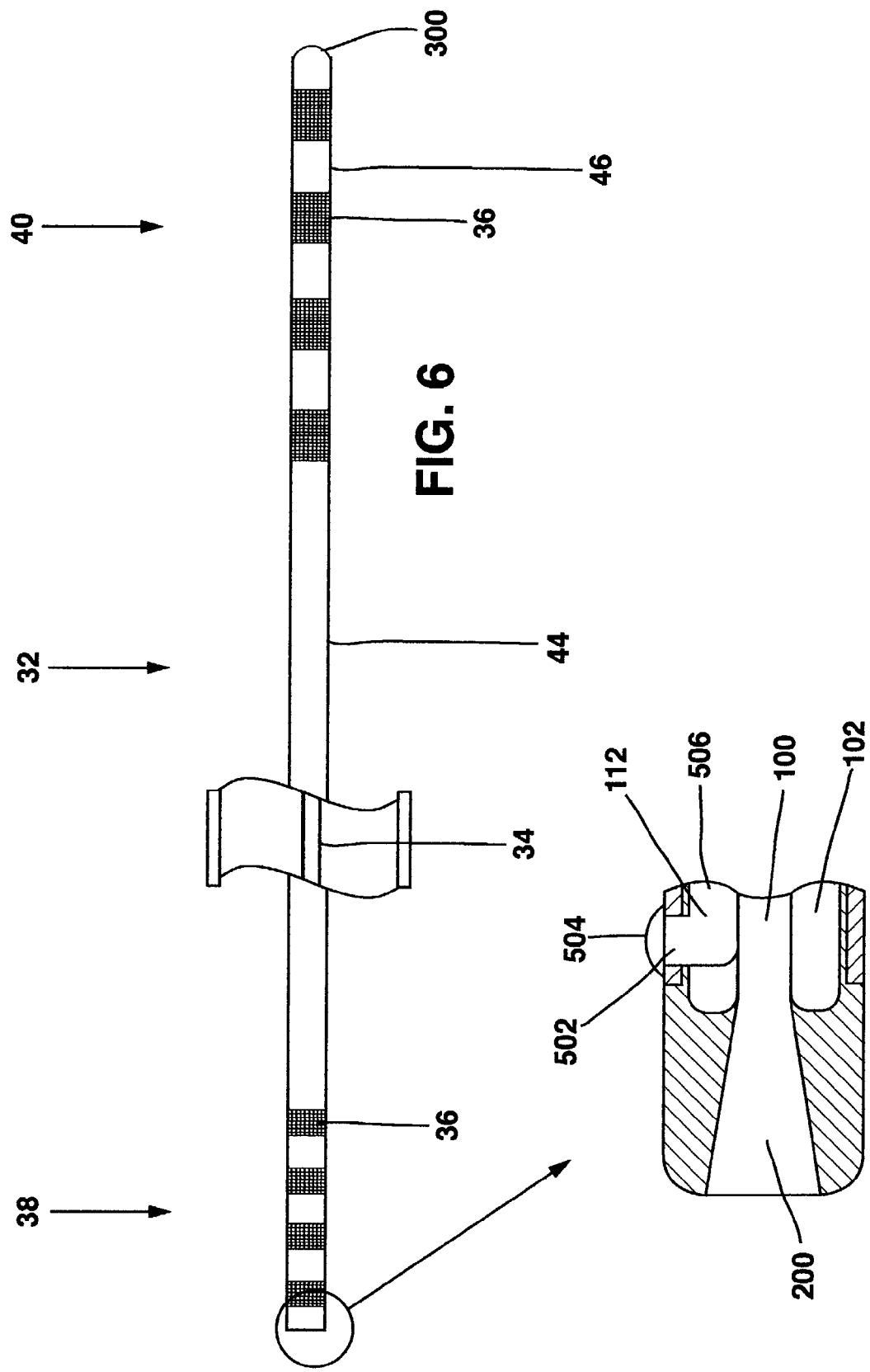

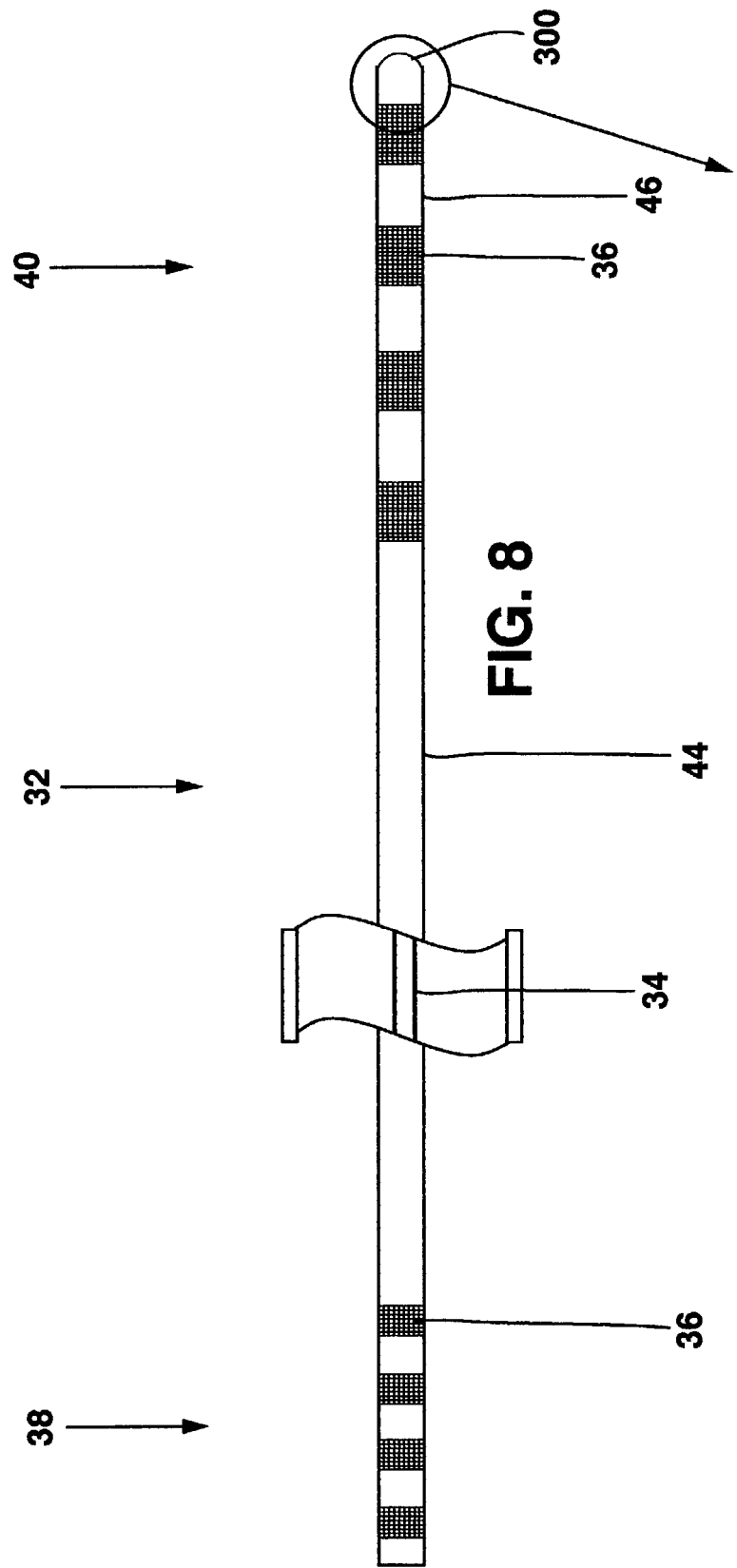
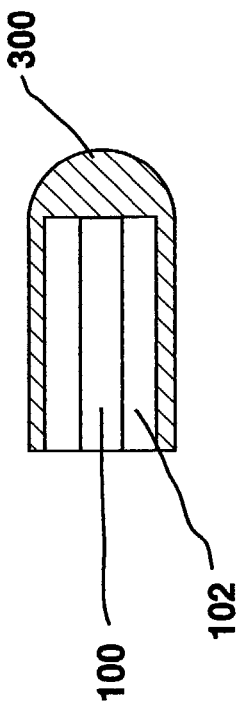
FIG. 8
FIG. 9

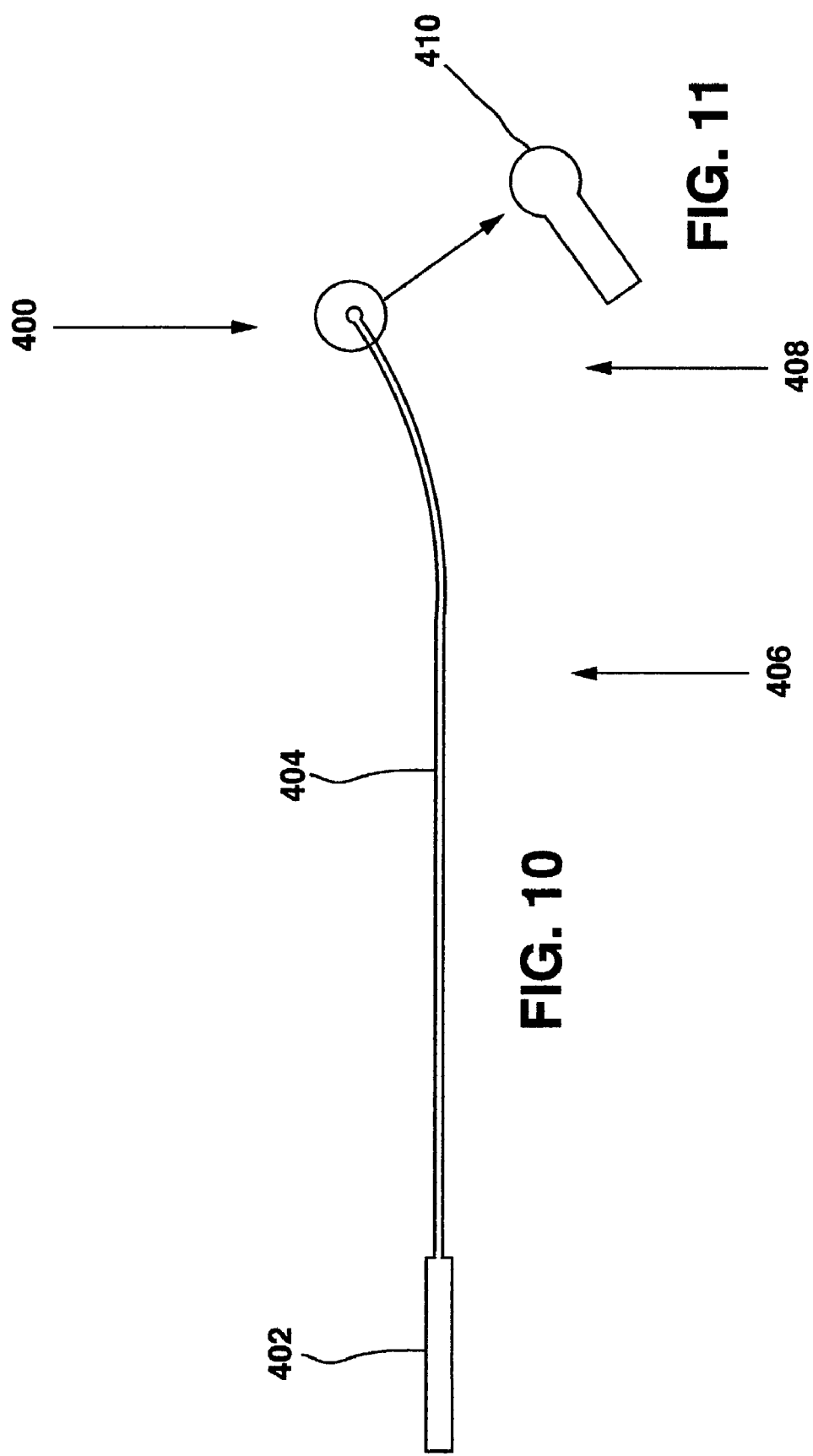

IMPLANTABLE LEAD WITH IMPROVED STYLET LUMEN

CROSS REFERENCES

This application is related to the following co-pending applications entitled "Implantable Lead With Improved Conductor Lumens" by Pardo et al. 10/128,884; "Implantable Lead With Improved Distal Tip" by Stolz et al. 10/128,934; "Improved Stylet For An Implantable Lead" by Pardo et al. 10/128,882; "Implantable Lead With Isolated Contact Coupling" by Pardo et al. 10/128,883; and, "Implantable Lead With Coplanar Contact Coupling" by Cole et al. 10/131,106, which are not admitted as prior art with respect to this application by its mention in this cross reference section.

BACKGROUND OF THE INVENTION

This disclosure relates to medical devices and more particularly to an implantable lead.

The medical device industry produces a wide variety of electronic and mechanical devices for treating patient medical conditions such as pacemakers, defibrillators, neurostimulators and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life. One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension such as shown in Medtronic, Inc. brochure "Implantable Neurostimulation System" (1998). More specifically, the neurostimulator system can be an Itrel II® Model 7424 or an Itrel 3® Model 7425 available from Medtronic, Inc. in Minneapolis, Minn. that can be used to treat conditions such as pain, movement disorders and pelvic floor disorders. The neurostimulator is typically connected to a stimulation lead that has one or more electrodes to deliver electrical stimulation to a specific location in the patient's body.

Clinicians often use a stylet to stiffen and steer the lead during implantation. The stylet is typically inserted in the lead proximal end through a stylet guide. Previous stylet guides are typically manufactured from a material that is harder than the lead body. When stylets are inserted or withdrawn from a hard stylet guide, the stylet can become bent or scratched potentially causing damage to the stylet lumen or the lead body. Additionally, previous hard stylet guides typically use a separate component to be added to the lead proximal end complicating manufacturing and creating a risk that the seal between the stylet guide and the lead proximal end could leak. An example of an optional stylet guide is shown in U.S. Pat. No. 6,216,045 "Implantable Lead And Method Of Manufacture" by Black et al. (Apr. 10, 2001). For the foregoing reasons, there is a need for an implantable lead with flared stylet lumen that reduces the potential for damage to a stylet and seals the lead proximal end.

BRIEF SUMMARY OF THE INVENTION

An implantable lead with improved stylet lumen reduces the potential for damage to a stylet and seals the lead proximal end. The implantable lead comprises a lead body having a distal end and a proximal end, a stylet lumen, at least two conductor lumens, at least two conductors, at least two contacts carried on the proximal end, at least two contacts carried on the distal end, and a proximal flare formed on the lead proximal end. The two conductors are contained in the conductor lumens and extend from the lead proximal end to the distal end. The two contacts carried on the lead distal end are electrically connected to the conductors. The proximal flare has tapering walls that narrow toward a stylet opening to guide insertion of a stylet into the stylet lumen, and the proximal flare seals the conductor lumens proximal end to isolate the conductor lumens.

BRIEF DESCRIPTION OF THE DRAWINGS

FIG. 4 shows an implantable lead with cross-section indication embodiment;

FIG. 5 shows a cross section of the implantable lead embodiment shown in FIG. 4;

FIG. 6 shows an implantable lead with proximal end enlargement indication embodiment;

FIG. 7 shows an enlarged cross section of the proximal end shown in FIG. 6;

FIG. 8 shows an implantable lead with distal end enlargement indication embodiment;

FIG. 9 shows an enlarged cross section of the distal end shown in FIG. 8 embodiment;

FIG. 10 shows a stylet with distal end enlargement indication embodiment;

FIG. 11 shows the enlarged distal end shown in FIG. 10 embodiment;

DETAILED DESCRIPTION OF THE PREFERRED EMBODIMENTS

Figure 1:
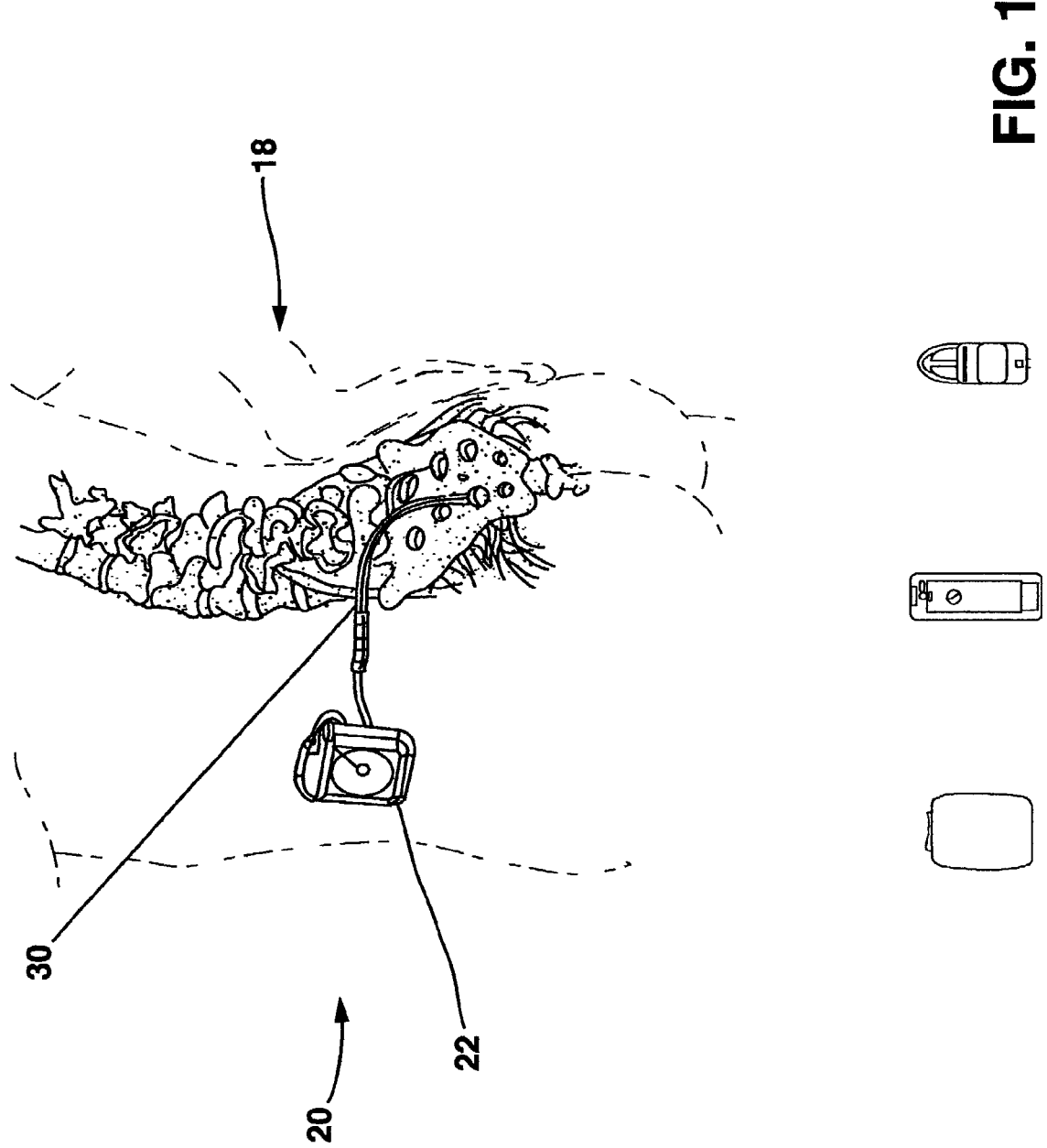
FIG. 1 shows a general environmental view for a neurostimulation system embodiment.
Figure 2:
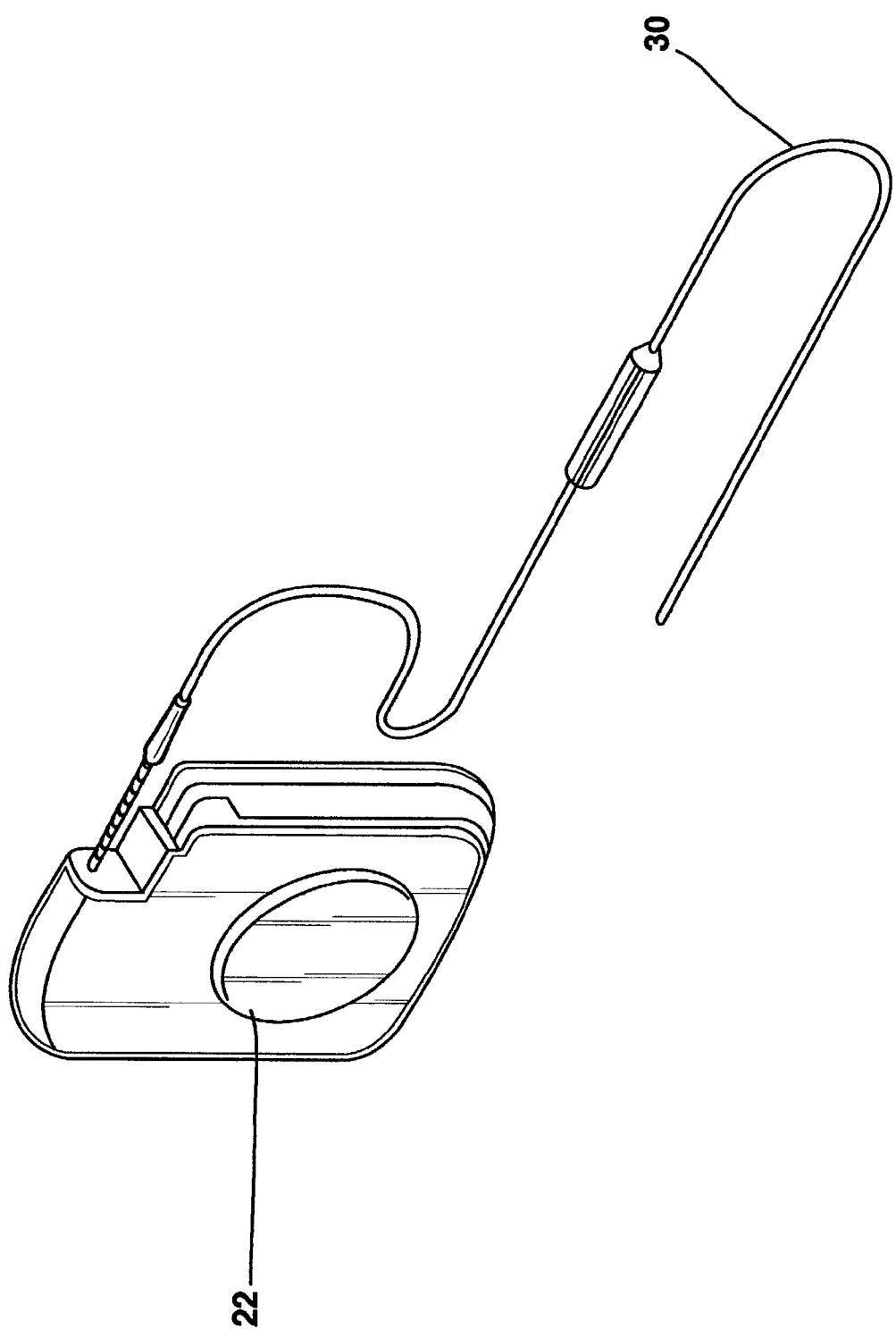
FIG. 2 shows a neurostimulation system embodiment.

FIG. 1 shows a general environmental view of an implantable neurostimulation system embodiment and FIG. 2 shows a neurostimulation system embodiment. Neurostimulation systems are used to treat conditions such as pain, movement disorders, pelvic floor disorders, gastroparesis, and a wide variety of other medical conditions. The neurostimulation system 20 includes a neurostimulator 22 such as an Itrel II®

Model 7424 or an Itrel 3® Model 7425 available from Medtronic, Inc. in Minneapolis, Minn., a stimulation lead extension 24, and a stimulation lead 30. The neurostimulator 22 is typically implanted subcutaneously in the patient's body 18 at a location selected by the clinician. The stimulation lead 30 is typically fixed in place near the location selected by the clinician using a device such as the adjustable anchor. The implantable lead 30 can be configured as a neurological stimulation lead, a neurological sensing lead, and a combination of both as a neurological stimulation and sensing lead, a cardiac lead, and the like.

Figure 3:
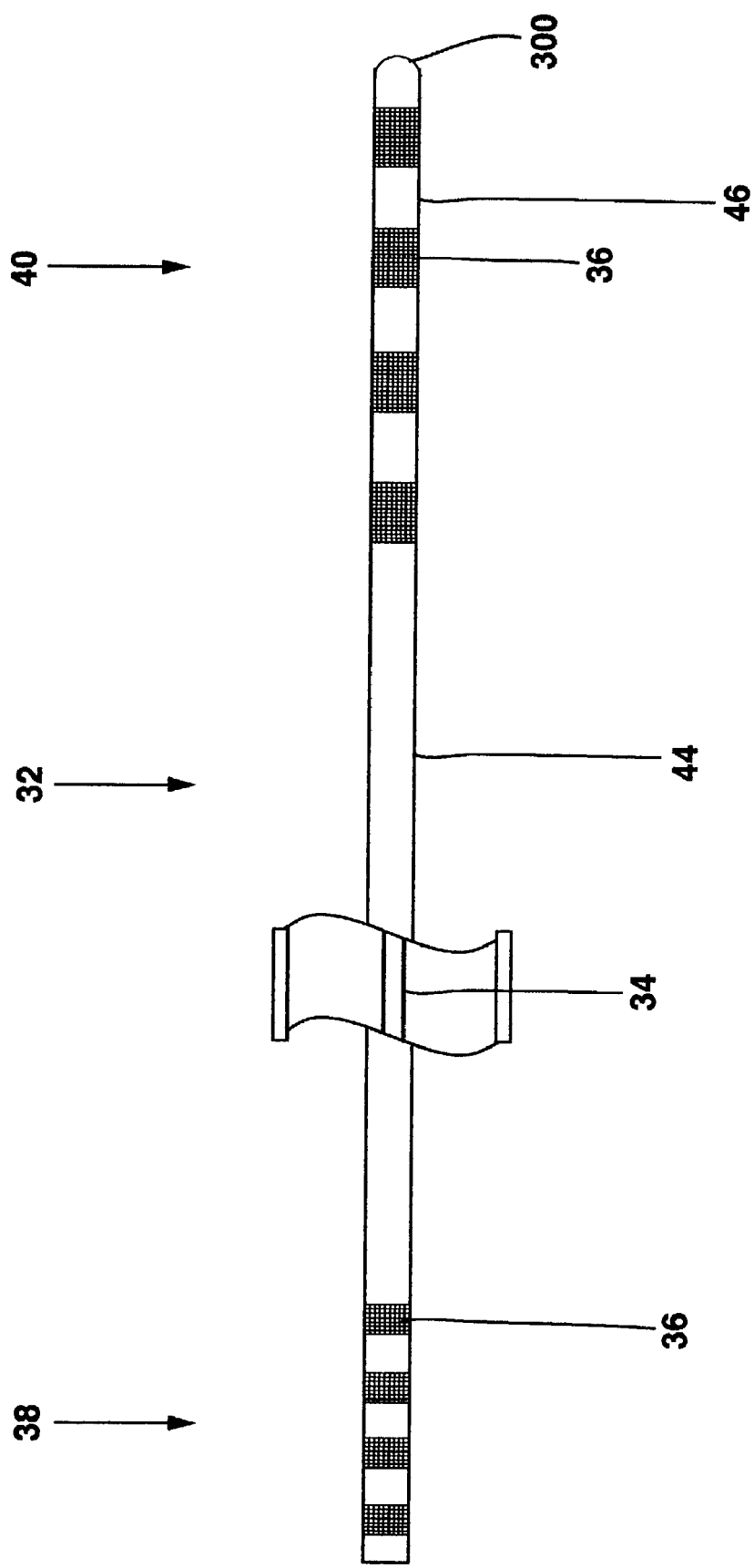
FIG. 3 shows an implantable lead embodiment.

FIG. 3 shows an implantable lead embodiment. An implantable lead comprises a lead body 32, at least one conductor 34, at least two contacts 36. The lead body has a proximal end 38, a distal end 40, and an exterior surface 44. The lead body 32 can be composed of a wide variety of electrically isolative materials and configurations. Materials may include, but are not limited to, silicone rubber, polyurethane, fluoropolymers and the like. Configurations could include monolumen and multilumen lead bodies. The exterior surface 44 is composed of one or more biocompatible materials.

The conductor 34 is contained in the lead body and generally extends from the lead proximal end 38 to the distal end 40. The conductors 34 can be manufactured from a wide range of materials that are electrically conductive such as MP35N, platinum and the like. In some embodiments, the conductor 34 can comprise a plurality of wires that can be configured as braided strand wire (BSW). BSW is available in many configurations including seven wire BSW. When low impedance is desired, the core of each wire can be manufactured from a low impedance metal such as silver and the jacket can be manufactured from a material with good mechanical strength properties such as MP35N. One embodiment of conductor 34 uses seven wire BSW with a silver core and an MP35N jacket typically with a resistance of less than about 0.098 ohms/cm (3 ohms/foot) and a tensile strength greater than 5N. The conductor 34 can be electrically insulated with a flouro-polymer such as ethyletetraflouroethylene with a coating thickness of approximately 0.0002 cm (0.0008 inch).

The contacts 36 includes at least one contact 36 carried on the lead distal end 40 that is electrically connected to the conductor 34 and at least one contact 36 carried on the proximal end 38 that is electrically connected to the conductor 34. The proximal contacts are typically manufactured from a material with good mechanical strength and biocompatible properties such as MP35N and the like to withstand interaction with mating devices such as an implantable neurological extension. The distal contacts are typically manufactured from materials with good electrical and biocompatibility properties such as platinum and iridium alloys that can be configured in a mixture such as 90% platinum and 10% iridium. In some embodiments, spacers 46 are inserted between contacts 36 so the proximal end 38 and distal end 40 are substantially iso-diametric.

FIG. 4 shows an implantable lead embodiment, and FIG. 5 shows a cross section of the implantable lead in FIG. 4. An implantable lead with improved conductor lumens comprises a lead body 32, a stylet lumen 100, at least one conductor lumen 102, and at least one axial slit 42. The lead body has an internal portion 104 and an external portion 106. The stylet lumen 100 and the conductor lumen 102 are formed in the internal portion 104. The internal portion 104 is a continuous material that has a proximal end 38, distal end 40 and an outer surface that is encapsulated by the external portion 104. This structure can be extruded and its configuration can be substantially the same at any longitudinal cross section. The internal portion 104 has an outside diameter smaller than the inside diameter of the external portion 106. In some embodiments, the internal portion 104 outside diameter is approximately 0.102 cm (0.04 inch) smaller than the external portion 104 inside diameter. The internal portion 104 is fitted inside of the external portion 106. The external portion 106 exterior surface 44 typically has an outer diameter selected for the therapeutic application such as in the range from about 0.05 cm (0.02 inch) to about 0.20 cm (0.08 inch) with one embodiment having an outer diameter of about 0.127 cm (0.05 inch). The stylet lumen 100 is formed in the internal portion 104 typically in the center and sized to provide clearance between the stylet lumen 100 and the coaxially inserted stylet wire 404 in the range from about 0.00025 cm (0.0001 inch) to about 0.025 cm (0.01 inch), and in some embodiments that clearance is about 0.0038 cm (0.0015 inches).

The conductor lumen 102 is formed in the internal portion 104 and positioned near an outer surface of the internal portion 104 such that there is only a web 110 between the conductor lumen 102 and the outer surface of the internal portion 104. Some embodiments have a plurality of conductor lumens 102 such as in the range from about two to sixteen conductor lumens 102. The implantable lead embodiment shown has four conductor assembly lumens that are substantially equidistant from each other and to the centrally localized stylet lumen. The conductor lumens 102 and stylet lumen 100 geometry provides axial stability, and the centrally located stylet lumen 100 improves navigation. Each conductor lumen 102 can be configured to resemble a polygon that is not necessarily symmetrical, and each conductor lumen 102 has a diameter typically greater than about 0.0254 cm (0.01 inch). In some embodiments, the conductor lumens 102 electrically insulate each conductor 34 and physically separate each conductors 34 to facilitate identification of the conductor 34 that is appropriate for its single corresponding contact 36. The film 108 thickness between the conductor lumens 102 and the stylet lumen 100 is no less than about 0.00254 cm (0.001 inch). This film 108 is flexible enough to allow the entering stylet to slide through the lead body without penetrating through into a conductor lumen 102 or out of the lead body.

The web 110 allows an axial slit 42 to be created in the internal portion 104 distal end for a path to exist between the conductor lumen 102 and the internal portion 104 outer surface. The web 110 is no greater than 0.005 cm (0.002 inch) thick. The web 110 provides the means for a conductor lumen 102 formed inside the lead body to be positioned near the exterior surface 44 of the lead body. The axial slit 42 is formed in the internal portion 104 distal end between the conductor lumen 102 and the outer surface of the internal portion 104. The axial slit 42 provides a temporary opening for a coupling 112 (FIG. 9) to exit the conductor lumen 102 and attach to a contact 36. The axial slit 42, when stretched ajar, opens to a width of at least about 0.01 cm (0.0039 inch) to allow the coupling 112 to exit the conductor lumen 102. Once the coupling 112 is connected to the contact 36, the axial slit 42 preferably seals back.

FIG. 6 shows an implantable lead with proximal end 38 enlargement indication embodiment, and FIG. 7 shows an enlarged cross section of the proximal end 38 shown in FIG. 6. An implantable lead with improved stylet lumen comprises a lead body, at least two conductors 34, contacts 36, and a proximal flare 200. The lead body has a proximal end 38, a distal end 40, a stylet lumen 100, and at least two conductor lumens 102. The conductors 34 are contained in the conductor lumens 102 extending from the lead proximal end 38 to the distal end 40. The contacts 36 are carried on the distal end 40 and electrically connected to the conductors 34. Typically, conductors 34 are also carried on the proximal end 38 and electrically connected to the conductors 34.

The proximal flare 200 is formed on the lead body proximal end 38 and it has tapering walls that narrow toward a stylet opening to guide insertion of a stylet (FIG. 10) into the stylet lumen 100, and the proximal flare 200 seals the conductor lumens 102 proximal end to isolate the conductor lumens 102. The proximal flare 200 is manufactured for a non-rigid material typically similar to the lead body material. The tapering walls have a slope typically in the range from about 0.25 cm/cm to about 0.50 cm/cm. The axial length of the flare 200 is no greater than about 0.064 cm (0.025 inches). The wall thickness of the flare 200 ranges from 0.01 cm (0.004 inch), at the most proximal end, to 0.05 cm (0.019 inch), at the distal end of the flare 200. The proximal flare 200 is flexible to reduce stylet deformation during insertion or withdrawal of the stylet. During stylet insertion into the stylet lumen 100, navigation, and withdraw, the tapered walls absorb energy and stretch to accommodate movement of the stylet to reduce stylet deformation. Also during stylet insertion into the stylet lumen 100, the proximal flare 200 substantially prevents the stylet from entering the conductor lumens 102. The flare 200 provides a progressive tactile feedback to indicate to the clinician the amount of of stylet pressure being applying to the lead proximal end 38 which reduces lead/stylet damage or deformation during implant.

The proximal flare 200 seals the conductor lumens 102 proximal end to isolate the conductor lumens 102. The forming of the flare 200 places material in the conductor lumens 102 that typically extends no farther than the beginning of the conductors 34 located within the conductor lumens 102. Sealing the conductor lumens 102 minimize electrical conductance between the conductors 34, fluid migration into the lumens or other attached neurological devices, and unwanted stylet introduction into the conductor lumens 102. The proximal flare 200 is manufactured from a non-rigid material that can be the same material as the lead body. The flare 200 can be formed by inserting the proximal end 38 of the lead body into a mold that has a conical shape. This conical shape is inserted axially into the center stylet lumen 100. Heat is transferred from the conical mold to the polyurethane internal portion 104 that seals the outer lumens and creates the flare 200.

FIG. 8 shows an implantable lead with distal end 40 enlargement indication embodiment, and FIG. 9 shows an enlarged cross section of the distal end 40 shown in FIG. 8. An implantable lead with an improved distal tip 300 comprises a lead body, at least two conductors 34, contacts 36, a stylet lumen 100, conductor lumens 102, and a distal tip 300. The lead body has a proximal end 38, a distal end 40, a stylet lumen 100, and at least two conductor lumens 102. The at least two conductors 34 contained in the conductor lumens 102 extending from the lead proximal end 38 to the distal end 40. The at least two contacts 36 carried on the proximal end 38 are electrically connected to the conductors 34. The at least two contacts 36 carried on the lead distal end 40 are also electrically connected to the conductors 34.

The formed distal tip 300 seals the conductor lumens 102 free from adhesive or solvents. The conductor lumens 102 closed off by the formed distal tip 300 improve electrical isolation between the conductors 34. The formed distal tip 300 penetrates the lumens 100, 102 of the lead body. The material filling reaches no further into the lumens than making contact to the enclosed conductors 34.

The distal tip 300 can be formed from the lead body by inserting into a mold; this mold has the shape of the desired distal tip 300. The distal tip 300 has a diameter approximately equal to the lead final diameter of approximately 0.127 cm (0.05 inch). The heat conducted from the mold to the lead distal tip 300, melts the surrounding material into the conductor lumen 102 and into the stylet lumen 100, completely sealing them from the outside. Sufficient material is left between the lumens 100, 102 to the outside of the lead such that substantial force would be needed to perforate, if at all, through the finally formed distal tip 300. The formed distal tip 300 is of the same material of the lead body and significantly minimizes the possibility of separation from the lead body.

The distal tip 300 is substantially symmetrical since there is no need to align a separate distal tip 300. The distal tip 300 is symmetrically formed such that it is coaxial with the lead body. Symmetry is desirable for minimized protuberances from the exterior lead surface 44, thus reducing the potential of lead body ruptures. The symmetrical formation of the distal tip 300 also reduces physical and material discontinuities in the distal tip 300 to improve the navigational sensitivity of the lead 30 during implant potentially reducing operating room time.

The distal tip 300 is a more robust stylet stop which reduces the opportunity for stylet penetration of the lead body distal end 40. The material penetrates the most distal end of the stylet lumen 100 by about 0.15 cm (0.059 inch) into the stylet lumen 100 of the lead beginning from the most distal end of the hemi-spherical distal tip 300. The force transfer required for perforation of the lead distal end 40 is significantly increased, therefore, reducing any potential of tissue damage due to an exiting stylet and reducing the potential of creating an opening in the lead which may disable electrical properties of the device.

FIG. 10 shows a stylet with stylet distal end 400 enlargement indication embodiment, and FIG. 11 shows the enlarged distal end shown in FIG. 10. An implantable lead with an improved stylet comprises a lead body, a stylet lumen 100, at least one conductor 34, contacts 36, and a stylet. The lead body has a proximal end 38, a distal end 40, an exterior surface 44, and a stylet lumen 100 contained inside the lead body. The conductor 34 is contained in the lead body and generally extends from the lead proximal end 38 to the distal end 40. The conductor 34 is electrically insulated by the lead body. There is at least one contact 36 carried on the lead proximal end 38 that is electrically connected to the conductor 34, and there is at least one contact 36 carried on the lead distal end 40 that is electrically connected to the conductor 34.

The stylet is composed of a stylet handle 402 that attaches to the proximal end 38 of the lead and a stylet wire 404. The stylet wire 404 is configured for insertion into the stylet lumen 100 with a straight portion 406, a curved portion 408, and a ball tip 410 on the stylet distal end 400. The straight portion of the lead has a diameter of about 0.0254 cm (0.01 inch) and has a parylene insulation of about 1.0 micron. The electrical insulation also serves as a coating that has a lower coefficient of friction than the stainless steel of the stylet wire 404.

The curved portion of the stylet wire 404 has an angle, between the tangent of the curved portion and the straight portion that increases as the curve approaches the stylet distal end 400. The curved portion begins at about less than 3.75 cm (1.48 inches) from the stylet distal end 400 of the stylet wire 404. The most distal angle of the curved portion has an angle greater than about 15 degrees from the straight portion.

The tangent of the curve with respect to the straight portion of stylet increases linearly as the curve approaches the stylet distal end 400. Once fully inserted into the lead, the stylet/lead results in a distal end angle that allows the physician to manipulate the device into the desired location over the epidural space. The continuous and incremental curve of the lead distal tip 300 aids the physician to guide the lead past anatomical obstructions, that would otherwise, hinder the ease of introduction of the lead to its designated location for stimulation.

The ball tip 410 is spherical and has a diameter that is greater than the stylet diameter and is no greater than the stylet lumen 100 inner diameter. The ball tip 410 is configured to ease insertion of the stylet wire 404 through the stylet lumen 100 to the stylet distal end 400. The ball tip 410 functions by stretching the lumen where the stylet wire 404 is inserted to ease insertion of the remaining portion of the stylet wire 404. In addition, the ball tip 410 reduces abrasion to the stylet lumen 100 to reduce the risk of the stylet wire 404 protruding into the adjacent conductor lumens 102 or out of the exterior surface 44 of the lead body.

Figures 12, 13:
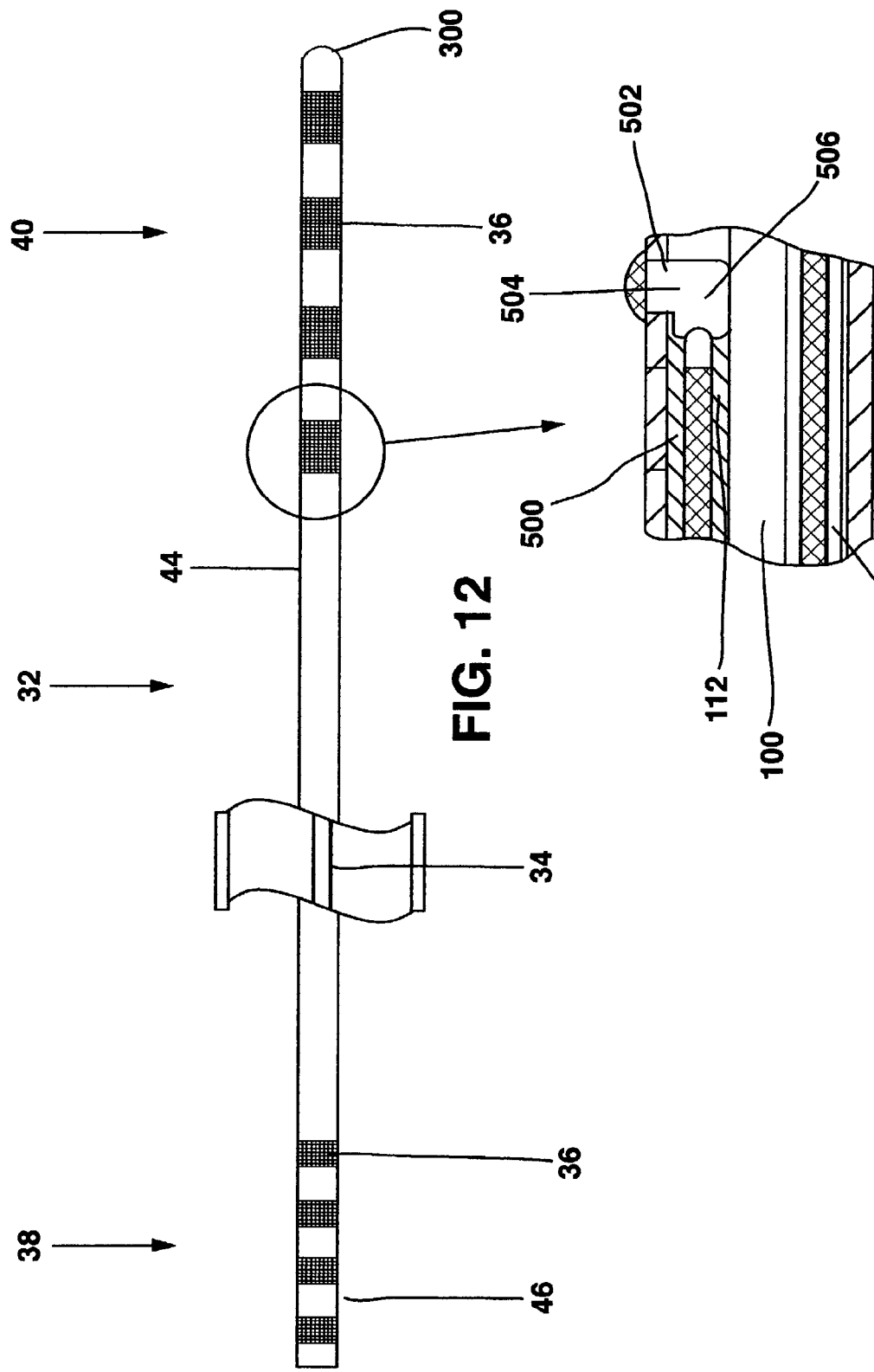
FIG. 12 shows an implantable lead with enlargement indication of a contact embodiment.
FIG. 13 shows a cross section of the enlarged contact embodiment.

FIG. 12 shows an implantable lead with contact 36 enlargement indication, and FIG. 13 shows a cross section of an enlarged contact 36 embodiment. The coupling 112 has a conductor coupling 500 and a contact coupling 502. The conductor coupling 500 and the contact coupling 502 are manufactured from a material with good mechanical and electrical properties such as MP35N and the like. The conductor coupling 500 is placed over the conductor 34 and attached to the conductor 34 mechanically. The contact coupling 502 exits the lead body and has a weld 504 to connect the contact coupling 502 to the contact 36. The weld 504, such as a laser weld, can be performed substantially on the contact 36 exterior surface 44 for ease of manufacturing. The weld 504 is performed such that the weld 504 pool is typically contained within the contact 36 perimeter. In addition, the weld 504 height is controlled to be less than about 0.0127 cm (0.005 inch), so interaction with other devices is facilitated. Each contact 36 has a contact slot 508 opening that in some embodiment is in the range from about 0.0127 cm (0.005 inch) to about 0.0381 cm (0.015 inch) in width and at least about 0.0508 cm (0.020 inch) in length. In other embodiments, the contact slot 508 can extend the entire length of the contact 36.

An isolation space 506 is created between the conductor 34 and the contact 36 to prevent directly welding the conductor 34 to the contact 36. The isolation space 506 separates the conductor 34 from the weld 504 to substantially prevent the conductor 34 from contacting the weld 504. The isolation space 506 is necessary since silver is not wanted in the weld 504 pool because silver potentially weakens the strength and integrity of a weld 504. In addition, it is desirable to avoid having silver contact the outside surface of the lead to avoid any direct contact with tissue. Although silver contact with tissue is not considered harmful, the separation serves as an additional precaution. The isolation space 506 is greater than about 0.05 cm (0.02 inch). The isolation space 506 serves as a means for isolation created between the conductor 34 and the contact 36 to prevent directly welding the conductor 34 to the contact 36. In some embodiments, the isolation space can include a fill material such as epoxy.

Figure 15:
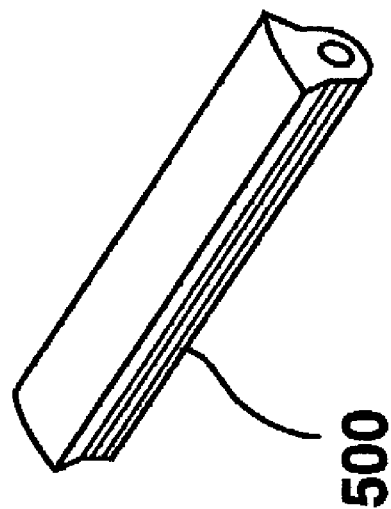
FIG. 15 shows an isometric view of the coupling embodiment shown in FIG. 14.
Figure 14:
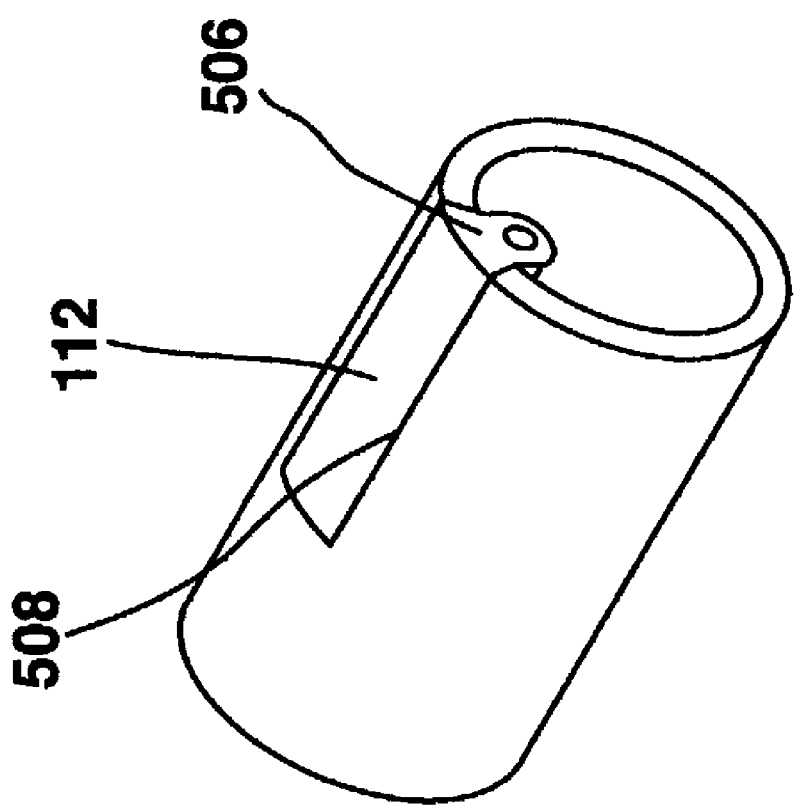
FIG. 14 shows an isometric view of a contact and coupling embodiment.

FIG. 14 shows an isometric view of a contact 36 and coupling 112 embodiment, and FIG. 15 shows an isometric view of the coupling 112 embodiment shown in FIG. 14. In this embodiment, the isolation space 506 is provided by the specific geometry of the contact coupling 502 and more specifically the non-welded material between the conductor 34 and the weld 504 to the contact 36. The non-welded material is sized appropriately for the dimensions of the lead such as greater than about 0.005 cm (0.002 inches). In this embodiment, the interface between the outer surface of the contact 36 and the other surface of the coupling 500 can be continuously welded along selected sides of the interface or intermittently welded along the interface.

Figure 16:
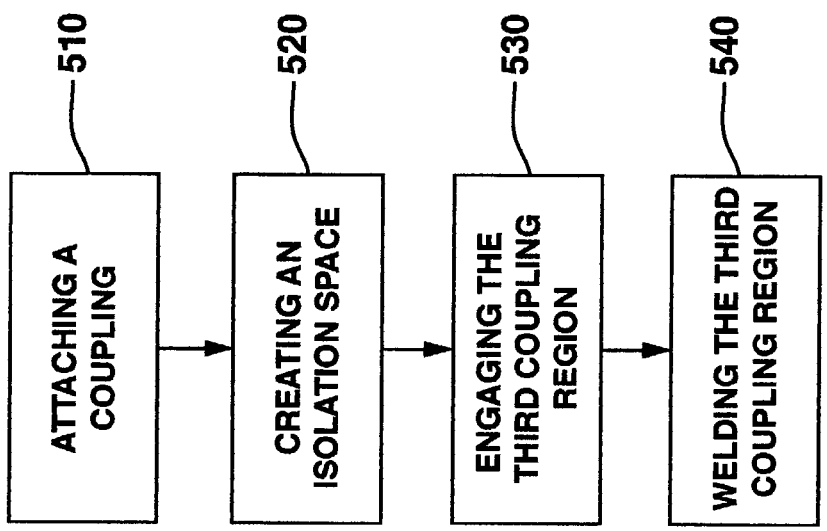
FIG. 16 shows a flow chart of a method for creating an isolation space in an implantable lead contact connection embodiment; and, FIG. 17 shows a flow chart of a method for creating a coplanar connection in an implantable lead between a conductor and a contact embodiment.

FIG. 16 shows a flow chart of a method for creating an isolation space 506 in an implantable lead contact connection embodiment. The method for creating an isolation space 506 comprises the following elements. A coupling 112 is attached 510 to a conductor 34 so that the conductor 34 extends into a first coupling region 500 of the coupling 112. The coupling 112 has a second coupling region 506 that is adjacent to the first coupling region 500 and a third coupling region 502 adjacent to the second coupling region 506. An isolation space 506 is created 520 and formed by the second coupling region 506. The isolation space 506 is void of the conductor 34. The third coupling region 502 is engaged 530 into a contact slot 508 formed in a contact 36. The third coupling region 502 is welded 540 to the contact 36 creating a contact weld 504.

In the coupling 112 embodiment shown in FIG. 13, the method for creating an isolation space 506 in an implantable lead contact connection is performed as follows. A coupling 112 is attached to a conductor 34 distal end so that a first coupling region 500, a second coupling region 506, and a third coupling region 502 are formed. The first coupling region 500 is mechanically attached to the conductor 34 in a crimping process that substantially reduces the diameter of the first coupling region 500 such that it engages the conductor 34 firmly. During mechanical attachment, the crimping force is adjusted to obtain an adequate pull strength while avoiding undesired damage/deformation to the wire 404. The conductor 34 distal end extends into the first coupling region 500 of the coupling 112. The second coupling region 506 is distal to the first coupling region 500, and the third coupling region 502 is distal to the second coupling region 506. The first region can be about 0.10 cm (0.04 inch) long, the second region can be about 0.05 cm (0.02 inch) and the third region can be about 0.076 cm (0.03 inch) long. An isolation space 506 is created and formed by the second coupling region 506, with the isolation space 506 void of the conductor 34. The isolation space 506 is void of the conductor 34 so that the weld 504 encompasses the third region and the contact 36.

The assembly consisting of the conductor 34 and the attached couplings 112 on either end can be fed through a lead body. The placement of the assembly is such that the proximal coupling is on the proximal end 38 of the lead body and the distal coupling is on the distal end of the lead body. The contact 36 with a contact slot 508 is placed on the lead body distal end. The contact slot 508 width is slightly less than the diameter of the third coupling region 502. The length of the contact slot 508 is greater than the diameter of the coupling 112 to allow for placement anywhere along its length. The contact slot 508 assists in holding the coupling 112 in place prior to welding the third region to the contact 36.

An axial slit 42 is created in the lead body distal end. The axial slit 42 is long enough such that it allows for an opening of at least the diameter of the third coupling region 502. The coupling 112 attached to the conductor 34 is exited through the axial slit 42 in the lead body distal end. The axial slit 42 permits the coupling 112 to pass through to mate to the contact 36 with the minimum amount of movement of the conductor 34 assembly within the lead body. Also, the axial slit 42 allows for a minimum sized path to exist between the conductor lumen 102 and the contact 36. In the creation of the axial slit 42, material is not removed, only a cut is made such that it allows the passage of the coupling 112 from the conductor lumen 102 to the contact slot 508 area. The cut is created with a sharp razor and extends for about 0.076 cm (0.030 inch). It is made approximately under the location where the contact 36 will be placed over and mate with the coupling 112.

The third coupling region 502 is bent in the range from about 85 degrees to about 120 degrees in relation to the longitudinal axis of the conductor 34. The bend can be made with a tool the size of a wrench that creates a bend beginning at the same location of the coupling 112, roughly 0.076 cm (0.03 inch) distally. The third coupling region 502 distal end is formed into a contact coupling 502 that is complimentary to a contact slot 508. The diameter of the third coupling region 502 is deformed such that it closes the conductor 34 void opening of the third coupling region 502. Also, the formed final geometry of the third region of the coupling 502 has an interference fit with the contact slot 508.

The contact coupling 502 is engaged into the contact slot 508. The entire perimeter and cross section of the third region 502 is placed within the open area of the contact slot 508. At this point the third coupling region 502 is held by the contact slot 508 and is ready for a more secure attachment. The contact coupling 502 is welded to the contact slot 508. The weld 504 can be created with a laser welder that heats up the slot 508 region of the contact 36 and the third region of the coupling to the point where they become an alloy. The weld 504 bump created is no greater than about 0.013 cm (0.005 inch) over the surface of the contact 36. Also, the weld 504 bridges over each end of the slot 508 to provide mechanical integrity. The inner void of the third coupling region 502 distal end is sealed by the weld 504. The weld 504 surface area extends over the third region 502 of the coupling and the proximate perimeter of the contact slot 508. The weld 504 material creates a closed section in the third region 502 opening creating a closed section of the coupling distal end (third coupling region 502).

FIG. 12 shows an implantable lead with contact enlargement indication, and FIG. 13 shows a cross section of an enlarged contact embodiment. An implantable lead with coplanar contact connection comprises a lead body having a proximal end 38 and a distal end 40, at least one conductor 34, at least one contact 36 carried on the proximal end 38, at least one contact 36 carried on the distal end 40, and at least one coupling 112. The lead body 32 has an exterior surface 44. The conductor 34 is contained in the lead body 32 and extends generally from the lead proximal end 38 to the distal end 40. The conductor 34 is electrically insulated. There is at least one contact 36 carried on the proximal end 38 that is electrically connected to the conductor 34, and at least one contact 36 carried on the distal end 40 that is electrically connected to the conductor 34. The coupling 112 has a conductor coupling 500 and a contact coupling 502. The conductor coupling 500 is placed over the conductor 34 and attached to the conductor 34. The contact coupling 502 exits the lead body and is welded to connect the contact coupling 502 to the contact 36 carried on the distal end 40. The contact coupling 502 is further configured to exit the conductor lumen 102 and mate with the contact 36 while retaining the conductor 34 coplanar to the contact 36. The coplanar relationship between the conductor 34 and the contact 36 is such that the longitudinal axis of the conductor 34 is maintained substantially parallel to the longitudinal axis of the contact 36.

In some embodiments such as shown in FIG. 13, the contact coupling 502 can be bent to exit the conductor lumen 102 and mate with the contact 36 while maintaining the conductor 34 coplanar to the contact 36. The contact coupling 502 bend serves as a means for orienting the contact coupling 502 to exit the conductor lumen 102 and mate with the contact 36. The contact coupling 502 can be bent in the range from about 85 degrees to about 120 degrees in relation to the conductor 34. In other embodiments such as shown in FIGS. 14 and 15, the geometry of the contact coupling 502 is such that the contact coupling 502 does not require mechanical deformation of the second region 506 or third region 502.

The conductors 34 are contained within the lumens throughout the lead body, such that it does not exit the lead at any point. The conductor 34 is parallel to the lead body in its entire length. This allows the conductor 34 to not directly contact the outside surface of the lead or the surrounding tissue. Conductor 34 stresses are significantly reduced by not allowing the conductor 34 to have a bending moment. Lead reliability is improved as a result from this coplanar conductor 34 to contact 36 attachment.

Figure 17:
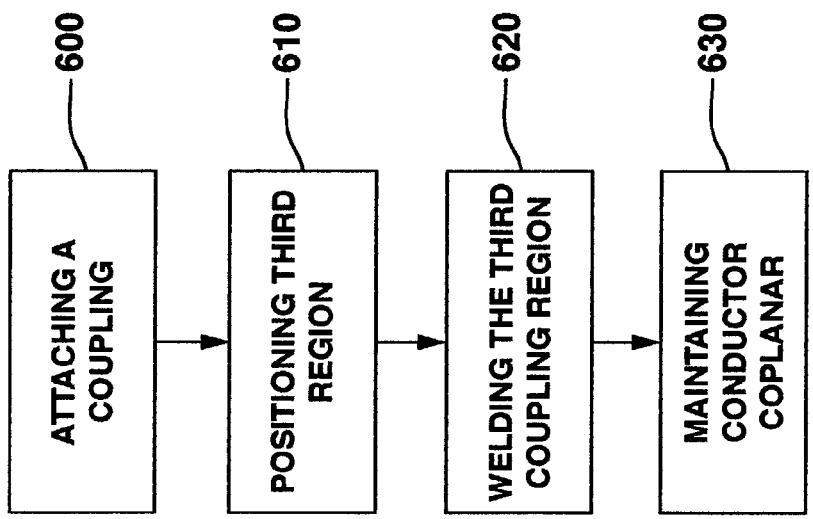

FIG. 17 shows a flow chart of a method for creating a coplanar connection in an implantable lead between a conductor 34 and a contact 36 embodiment. The method for creating a coplanar connection in an implantable lead between a conductor 34 and a contact 36 comprises the following elements. A coupling 112 is attached 600 to a conductor 34 distal end, so the conductor 34 distal end extends into a first coupling region 500 of the coupling. The coupling 112 has a second coupling region 506 adjacent to the first coupling region 500. The coupling second region 506 is positioned 610 in a conductor lumen 102 adjacent 620 to a contact 36. The second region 506 is welded 62 to the contact 36 creating a contact weld 504. The conductor 34 distal end is maintained in a coplanar relation 630 to the contact 36.

Thus, embodiments of the implantable lead with flared stylet lumen 100 are disclosed to seal the conductor lumen 102 proximal ends while improving stylet insertion. One skilled in the art will appreciate that the present invention can be practiced with embodiments other than those disclosed. The disclosed embodiments are presented for purposes of illustration and not limitation, and the present invention is limited only by the claims that follow

What is claimed is:

1. An implantable lead with improved stylet lumen, comprising:
    a lead body having a proximal end, a distal end, a stylet lumen, and at least two conductor lumens each having a proximal end;
    at least two conductors contained in the conductor lumens extending from the lead proximal end to the distal end;
    at least two contacts carried on the proximal end and electrically connected to the conductors;
    at least two contacts carried on the lead distal end and electrically connected to the conductors; and,
    a proximal flare formed on the lead body proximal end, the proximal flare having tapering walls that narrow toward a stylet opening to guide insertion of a stylet wire into the stylet lumen, and the proximal flare being formed to seal the proximal ends of the conductor lumens to electrically isolate the conductor lumens.

2. The implantable lead as in claim 1 wherein the proximal flare is flexible to reduce stylet wire deformation during use of the stylet.

3. The implantable lead as in claim 1 wherein the proximal flare is manufactured from the same material as the lead body.

4. The implantable lead as in claim 1 wherein the proximal flare substantially prevents the stylet from entering the conductor lumens upon insertion of the stylet in the lead body proximal end.

5. A method of manufacturing an implantable lead, comprising:
    extruding a lead body having a proximal end, a distal end, a stylet lumen, and at least two conductor lumens;
    extending at least two conductors within the conductor lumens from the lead proximal end to the distal end;
    coupling at least two contacts on the proximal end;
    connecting the at least two contacts on the proximal end to the conductors;
    coupling at least two contacts on the lead distal end;
    connecting the at least two contacts on the distal end to the conductors; and,
    forming a proximal flare on the lead body proximal end, the proximal flare having tapering walls that narrow toward a stylet opening to guide insertion of a stylet wire into the stylet lumen, and the proximal flare being formed to seal the proximal ends of the conductor lumens to electrically isolate the conductor lumens.

6. The method of claim 5, wherein the proximal flare seals the conductor lumens proximal end to isolate the conductor lumens.

7. The method of claim 6, further comprising the step of routing material into the conductor lumens no farther than the beginning of the conductors located within the conductor lumens during the forming of the flare.

8. The method of claim 7, wherein the material routed into the conductor lumens seals the conductor lumens to minimize electrical conductance between the conductors, fluid migration into the lumens, and unwanted stylet introduction into the conductor lumens.

9. The method of claim 8, wherein the proximal flare is manufactured from a non-rigid material similar to the lead body.

10. The method of claim 5, wherein the flare can be formed by inserting the proximal end of the lead body into a conical shape mold.

11. The method of claim 10, wherein the conical shape is inserted axially into the center stylet lumen.

12. The method of claim 11, wherein heat is transferred from the conical mold to an interior portion of the lead to seal the outer lumens and create the flare.

13. A method of manufacturing an implantable lead, comprising:
    providing a lead body having a proximal end, a stylet lumen, and a conductor lumen having a proximal end;
    sealing the proximal end of the conductor lumen to electrically isolate the conductor lumen, the step of sealing the proximal end of the conductor lumen to isolate the conductor lumen comprising forming a proximal flare on the proximal end of the lead body to seal the proximal end of the conductor lumen, the proximal flare having tapering walls that narrow toward a stylet opening to guide insertion of a stylet wire into the stylet lumen.

14. The method of claim 13 wherein the step of forming a proximal flare on the proximal end of the lead body includes placing material in the conductor lumen.

15. The method of claim 14 further comprising locating a conductor within the conductor lumen, the conductor having a proximal end, the step of forming a proximal flare on the proximal end of the lead body includes placing material in the conductor lumen no farther than the proximal end of conductor.

16. The method of claim 13 wherein the step of forming a proximal flare on the proximal end of the lead body includes molding the proximal end with a conically shaped mold.

17. The method of claim 16 wherein the step of forming a proximal flare on the proximal end of the lead body further includes inserting a conical shape axially into the stylet lumen.

18. The method of claim 17 wherein the step of molding the proximal end with a conically shaped mold includes transferring heat from the conically shaped mold to proximal end of the lead body.

19. The method of claim 18 wherein the lead body is formed of polyurethane, the step of molding the proximal end with a conically shaped mold includes molding the polyurethane.

20. The method of claim 19 wherein the lead body further has a distal end, the step of providing a lead body including extruding the lead body, the method further comprising:
    extending a conductor within the conductor lumen, the conductor having a proximal end and a distal end;
    coupling a proximal contact on the lead body;
    connecting the proximal contact to the proximal end of the conductor;
    coupling a distal contact on the lead body;
    connecting distal a contact to distal end of the conductor.

21. The method of claim 20 wherein the conductor lumens comprise at least two conductor lumens, and the conductor comprises at least two conductors.

22. An implantable lead, comprising:
    a lead body having a proximal end, a distal end, a stylet lumen, and at least two conductor lumens each having a proximal end;
    at least two conductors contained in the conductor lumens extending from the lead proximal end to the distal end;
    at least two contacts carried on the proximal end and electrically connected to the conductors;
    at least two contacts carried on the lead distal end and electrically connected to the conductors; and,
    a proximal flare formed on the lead body proximal end, the proximal flare having tapering walls that narrow toward a stylet opening to guide insertion of a stylet wire into the stylet lumen, and the proximal flare being formed to seal the proximal ends of the conductor lumens to electrically isolate the conductor lumens;
    the proximal flare formed by inserting the proximal end of the lead body into a conical shaped mold that is inserted axially into the stylet lumen and heated to seal the conductor lumens and create the flare.

23. The implantable lead of claim 22, wherein the proximal flare is manufactured from a non-rigid material similar to a lead body material.

24. The implantable lead of claim 22, wherein the tapering walls have a slope in the range from about 0.25 cm/cm to about 0.50 cm/cm.

25. The implantable lead of claim 22, wherein the proximal flare axial length is no greater than 0.064 cm.

26. The implantable lead of claim 22, wherein the proximal flare wall thickness ranges from 0.01 cm at the most proximal end to 0.05 cm at the distal end of the flare.

27. An implantable lead comprising:
a lead body having a proximal end, a stylet lumen having a stylet opening, and a conductor lumen having a proximal end;
a proximal flare formed on the proximal end of the lead body, the proximal flare having tapering walls that narrow toward the stylet opening to guide insertion of a stylet wire into the stylet lumen;
the proximal flare formed by thermally molding the proximal end of the lead body such that the conductor lumen is sealed as the proximal flare is molded.

28. The implantable lead of claim 27 wherein the conductor lumen comprises at least two conductor lumens.

29. The implantable lead of claim 28 further comprising:
at least two conductors contained in the conductor lumens extending from the lead proximal end to the distal end;
at least two contacts carried on the proximal end and electrically connected to the conductors;
at least two contacts carried on the lead distal end and electrically connected to the conductors.

30. The implantable lead of claim 29 wherein the thermally molding the proximal end of the lead body places material in the conductor lumens.

31. The implantable lead of claim 30 wherein thermally molding the proximal end of the lead body places material in the conductor lumen no farther than the proximal end of conductor.

32. The implantable lead of claim 27 wherein the proximal end of the lead body is thermally molded with a conically shaped mold.

33. The implantable lead of claim 27 wherein the lead body is formed of polyurethane.

* * * * *